US010551361B2

(12) United States Patent
Lim et al.

(10) Patent No.: US 10,551,361 B2
(45) Date of Patent: Feb. 4, 2020

(54) COLUMN FOR MICRO GAS CHROMATOGRAPHY

(71) Applicant: Kookmin University Industry Academy Cooperation Foundation, Seoul (KR)

(72) Inventors: Si-Hyung Lim, Seoul (KR); Janghyeon Lee, Seoul (KR)

(73) Assignee: KOOKMIN UNIVERSITY INDUSTRY ACADEMY COOPERATION FOUNDATION, Seoul (KR)

(*) Notice: Subject to any disclaimer, the term of this patent is extended or adjusted under 35 U.S.C. 154(b) by 204 days.

(21) Appl. No.: 15/668,810

(22) Filed: Aug. 4, 2017

(65) Prior Publication Data

US 2018/0321199 A1  Nov. 8, 2018

(30) Foreign Application Priority Data

May 8, 2017  (KR) .................. 10-2017-0057569

(51) Int. Cl.
  *G01N 30/60* (2006.01)
  *B01D 15/10* (2006.01)
  *G01N 30/18* (2006.01)
  *G01N 30/02* (2006.01)

(52) U.S. Cl.
  CPC ......... *G01N 30/6095* (2013.01); *B01D 15/10* (2013.01); *G01N 30/18* (2013.01); *G01N 2030/025* (2013.01); *G01N 2030/185* (2013.01)

(58) Field of Classification Search
  CPC ..................... G01N 30/60; G01N 30/6095
  See application file for complete search history.

(56) References Cited

U.S. PATENT DOCUMENTS

| 8,123,841 B2 | 2/2012 | Masel et al. |
| 8,132,443 B2 | 3/2012 | McGill et al. |
| 2015/0300998 A1* | 10/2015 | Suslick ............. G01N 30/48 422/527 |
| 2016/0266073 A1* | 9/2016 | Du ..................... G01N 30/6086 |

OTHER PUBLICATIONS

Office Action from Korean Intellectual Property Office of 10-2017-0057569, dated Aug. 16, 2018.
Hyunsung Kang, Ultra-miniaturized urine odor analysis platform based on micro gas chromatography, Master degree thesis, Dec. 19, 2016, pp. 1-53, Graduate School of Mechanic Design Engineering of Kookmin University, Seoul, Republic of Korea, English translation of abstract.

* cited by examiner

*Primary Examiner* — David M. Gray
*Assistant Examiner* — Andrew V Do
(74) *Attorney, Agent, or Firm* — STIP Law Group, LLC (57) ABSTRACT

Disclosed is a separation column for micro gas chromatography, having superior separation performance and including a microchannel formed on a substrate and having a serpentine shape, and bumps formed on the surface of the microchannel, wherein the bumps are alternately disposed to face each other on the surface of the microchannel. In the separation column for micro gas chromatography, a sufficient pressure drop occurs, and thus an interaction between a gas mixture to be analyzed and a stationary phase in the column sufficiently takes place, whereby individual gas components are efficiently separated from the gas mixture, discharged from the column, and detected.

3 Claims, 6 Drawing Sheets

COLUMN FOR MICRO GAS CHROMATOGRAPHY

CROSS-REFERENCE TO RELATED APPLICATIONS

This application claims the priority of the Korean Patent Applications NO 10-2017-0057569 filed on May 8, 2017, in the Korean Intellectual Property Office, the disclosure of which is incorporated herein by reference.

BACKGROUND OF THE DISCLOSURE

1. Technical Field

The present invention relates to a column for use in micro gas chromatography, and more particularly to a column for micro gas chromatography, which is able to efficiently separate individual gas components from a gas mixture to be analyzed through micro gas chromatography, whereby the gas components contained in the gas mixture are separated and discharged at predetermined retention time intervals and may thus be easily detected.

2. Description of the Related Art

A gas chromatograph is a device configured such that individual gas components contained in a gas mixture to be introduced are separated and discharged and thus qualitatively and quantitatively analyzed. In order to analyze gas components, gas chromatography is performed using a carrier gas, a sample injector, a gas separation column, and a detector. Here, the carrier gas, which is a mobile phase, may mainly include $He$, $N_2$, $H_2$, $Ar$, or $CO_2$.

Also, the gas separation column, suitable for use in separating individual gas components of a gas mixture, includes an inner packing material (inert), a solid support (typically made of a diatomaceous earth material), and a coated liquid stationary phase, and the introduced gas mixture and the carrier gas may be subjected to interactions such as adsorption or distribution with a packing material or a material applied on the wall of the column, whereby individual gas components are separated and discharged while the gas mixture is passed through the column.

Specifically, the time during which the peak of the analyte of the injected sample appears on the detector is referred to as a retention time. While the gas mixture passes through the column, individual gas components in the gas mixture have different retention times and are separated and discharged from the column.

Meanwhile, in order to use urine to diagnose bladder cancer or prostate cancer-related disease at an early stage, thorough research is ongoing into a non-invasive diagnosis method using gas chromatography-mass spectrometry (GC-MS). In particular, a diagnosis method using cancer-related biomarkers such as volatile organic metabolites (VOMs) of a urine specimen is under study.

Moreover, as the non-invasive diagnosis method, human exhaled breath analysis enables early diagnosis of disease of patients and monitoring of state of health depending on the type of volatile organic compound (VOC) contained therein. An alkane-based gas, which is a kind of VOC, is utilized as a biomarker for asthma, COPD and heart disease, and analysis of the biomarker in the exhaled breath is performed using a commercially available system such as a GC-MS system.

However, the commercially available system has a large size of several meters, is very expensive to the extent of tens of millions of won, requires a complex operation process and a large power consumption of 2 kW or more, and may be used only by qualified and trained professionals due to the difficulty of analysis procedures and methods. The column used for the commercially available system is longer than 10 m, and thus limitations are imposed on reducing the size thereof, and a long analysis time is required.

Hence, a micro gas chromatograph, which may be used even without professional knowledge by laypeople and is portable, is being developed through a MEMS process.

The present invention addresses a column for use in micro gas chromatography, the column being manufactured in various geometric shapes such as a circular shape, a rectangular shape, a serpentine shape, and the like. Unless the channel is blocked due to the coating material and the structural shape of the channel under the same column length and flow-rate conditions, the reaction time between gas molecules and a stationary-phase material in the column increases with an increase in the pressure drop, and thus the separation effect is expected to increase.

The prior techniques in the art to which the present invention belongs are briefly described, and the technical aspects of the present invention to be differentiated from the prior techniques are also described.

U.S. Pat. No. 8,123,841 (Feb. 28, 2012) discloses a micro-column for gas chromatography, in which the column has a serpentine shape in order to separate a gas mixture to be introduced and in which the ratio of a channel spacing to a column diameter is limited, thus facilitating the coating of the column with a stationary phase.

Also, U.S. Pat. No. 8,132,443 (Mar. 13, 2012) discloses a micro-column for gas chromatography, in which the column has a serpentine shape in order to separate a gas mixture to be introduced, each of upper and lower substrates is manufactured so as to have a semicircular cross-section, and the upper and lower substrates are attached to manufacture a column having a cross-sectional shape close to a circular shape. Here, the stationary-phase coating is performed before attachment of the upper and lower substrates.

The above prior techniques are similar to the present invention in terms of the column for use in micro gas chromatography, but are problematic because the contact time between the introduced gas mixture and the stationary phase is insufficient, making it difficult to clearly separate the gas components.

Culminating in the present invention, intensive and thorough research, carried out by the present inventors aiming to solve the problems encountered in the related art, resulted in the finding that the contact time between the introduced gas mixture and the stationary phase may be significantly increased by changing the surface shape of the column.

SUMMARY OF THE INVENTION

Accordingly, the present invention has been made keeping in mind the problems encountered in the related art, and the present invention is intended to provide a separation column for micro gas chromatography, which enables the efficient distribution of retention times of gases discharged to a detector from the separation column, that is, enables the quantitative and qualitative analysis of the separated gases in the detector.

The present invention provides a separation column for micro gas chromatography, comprising: a microchannel formed on a substrate and having any one shape selected from among a rectangular shape, a circular shape, and a serpentine shape; and bumps formed on the surface of the microchannel, wherein the bumps are alternately disposed to face each other on the surface of the microchannel.

In the separation column for micro gas chromatography according to the present invention, the microchannel may have a total length of 1.4 to 1.6 m, a channel width of 140 to 200 μm, and a channel depth of 300 to 450 μm.

In the separation column for micro gas chromatography according to the present invention, the ratio of the distance r2 between the top of the bumps and the wall of the microchannel and the height r1 of the bumps formed on the wall of the microchannel, that is, an r2/r1 ratio, may range from 1.0 to 1.5, and the ratio of the distance d between the bumps and the height r1 of the bumps formed on the wall of the microchannel, that is, a d/r1 ratio, may range from 3 to 5.

According to the present invention, a separation column for micro gas chromatography can maximize the separation efficiency of introduced gases, whereby the retention times of individual gas components can be more broadly distributed, thereby improving clarity and realizing accurate qualitative and quantitative analysis in a detector.

DESCRIPTION OF SPECIFIC EMBODIMENTS

Hereinafter, a detailed description will be given of a column for use in micro gas chromatography according to preferred embodiments of the present invention with reference to the appended drawings so that the present invention may be easily carried out by those skilled in the art to which the present invention belongs.

Throughout the drawings, the sizes or dimensions of the elements may be depicted as being larger or smaller than actual sizes in order to provide an easily understood description of the present invention, and furthermore, known constitutions are omitted so as to expose featured constitutions, and thus the present invention is not limited to such drawings.

In the following description of exemplary embodiments of the present invention, detailed descriptions of known functions and components incorporated herein will be omitted when the same may make the subject matter of the present invention unclear.

Specific structural and functional descriptions of embodiments and drawings of the present invention disclosed herein are only for illustrative purposes of the preferred embodiments of the present invention, and are not intended to represent all of the technical ideas of the present invention, and thus a variety of equivalents and modifications able to substitute therefor may be provided at the point of time of filing of the present invention.

Figure 1A:
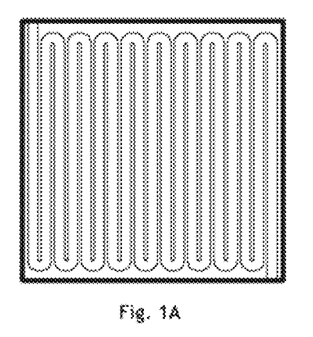
FIGS. 1A to 1C show examples of a microchannel of a micro gas chromatography column.
Figure 1B:
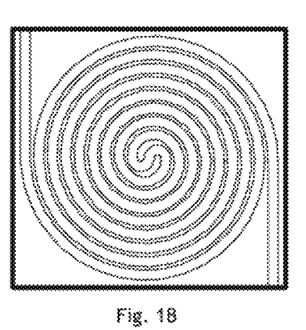
Figure 1C:
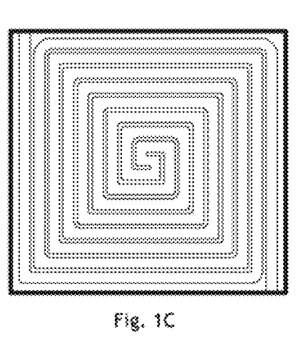

The present invention addresses a separation column for use in micro gas chromatography, including a microchannel formed on a substrate and having any one shape selected from among a serpentine shape (FIG. 1A), a circular shape (FIG. 1B), and a rectangular shape (FIG. 1C), and bumps formed on the surface of the microchannel, the bumps being alternately disposed to face each other on the surface of the microchannel.

Figure 2A:
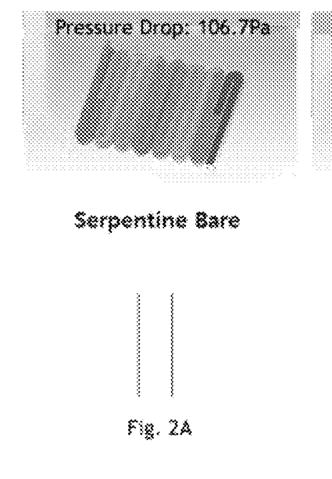
FIGS. 2A to 2C show the simulation results of a pressure drop depending on the structural shape of the micro gas chromatography column and the examples of the column structure.
Figures 2B, 2C:
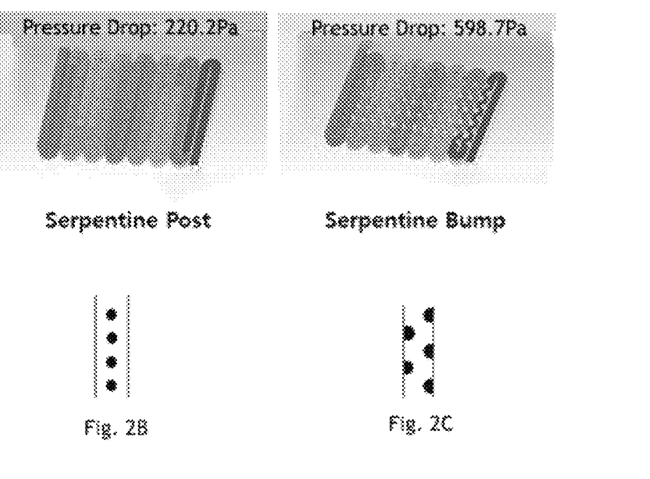

In the present invention, the serpentine shape, including the examples of the column shape illustrated in FIGS. 2A to 2C, is derived from the shape of a snake crawling on the floor, and is configured such that the fluid introduced into the microchannel flows linearly through a predetermined distance and then the direction of flow thereof is reversed.

The microchannel preferably has a channel width of 140 to 200 μm and a channel depth of 300 to 450 μm, but the present invention is not limited thereto.

As shown in FIGS. 2B and 2C, obstacles such as posts or bumps are formed on the surface of the serpentine microchannel, whereby a pressure drop, which is a pressure difference between the inlet pressure and the outlet pressure of the gas passing through the column or microchannel, may be increased. The posts may be formed by connecting the upper and lower surfaces of the channel at the center of the fluid flow of the channel, and the bumps may be alternately formed to face each other on opposite sides of the wall of the channel, but the present invention is not limited thereto. The serpentine shape is illustrated in FIGS. 2A to 2C, without being limited thereto, and the shape of the microchannel is any one selected from among a rectangular shape, a circular shape and a serpentine shape, and posts or bumps may be formed in the same manner on the selected microchannel.

As the pressure drop increases, the time during which the introduced fluid resides in the channel may also increase, and thus, when the structure that is able to cause a greater pressure drop is selected, the time at which the gas introduced into the micro gas chromatography column comes into contact with the stationary phase of the column increases, whereby the separation capacities of individual gas components of the gas mixture, that is, the retention times, are efficiently distributed, thus accurately analyzing the individual gas components in a detector.

Specifically, since the retention time cannot be directly checked through simulation before design and manufacturing of a micro gas chromatography column, based on the concept in which separation efficiently occurs depending on the extent of reaction between gas molecules to be separated and a stationary phase, better performance is expected with an increase in the pressure drop.

In order to optimize the design of the microchannel pressure drop in the column taking into consideration the geometric shape of the column and the flow rate and pressure of the gas, simulation analysis of a serpentine channel having the channel shape shown in FIGS. 2A to 2C is performed to evaluate the pressure drop for each shape, and an optimal column shape is determined therefrom.

To decide and design the model that satisfies these factors, the simulation is conducted using the ANSYS Fluent commercial analysis module prior to the manufacturing, the overall chip size being as follows: as shown in FIGS. 2A to 2C, a width of 20 mm, a length of 20 mm, a thickness of 625 μm, and the channel size of the column being as follows: a width of 150 μm, a depth of 400 μm and a length of about 1.5 m. To select a column having high separation performance, simulation is performed for a column having a geometric shape, for example, a column in which posts are formed at a regular interval on the surface of the channel (FIG. 2B), and a column in which bumps are alternately formed on opposite sides of the wall thereof (FIG. 2C), and the results of a pressure drop thereof are compared with those of a column (FIG. 2A) having no obstacles on the surface thereof.

The simulation was carried out under boundary conditions of an inlet flow rate of 1 SCCM and an outlet pressure of atmospheric pressure using a fluid such as air. In order to simulate the micro gas chromatography model, the width and depth of the channel matched the actual sizes, after which the length of the column was reduced to 1/100, and thus analysis was conducted.

Based on the simulation results of FIGS. 2A to 2C, the column having no obstacles on the surface thereof exhibited a pressure drop of 106.7 Pa, but the column having the posts and the column having the bumps manifested pressure drops of 220.2 Pa and 598.7 Pa, respectively. Accordingly, the column having the bumps can be found to realize a greater pressure drop even for a channel having the same length, and also to exhibit the highest gas mixture separation performance.

If the pressure drop is too low, interactions between the stationary phase and the gas mixture become insufficient, resulting in low separation performance. On the other hand, if the pressure drop is too high, clogging may occur in the microchannel, and a long analysis time and high operation costs are required.

Figure 3:
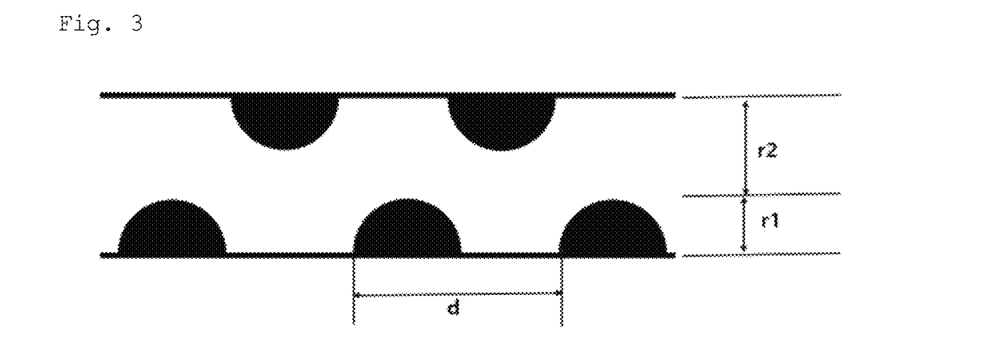
FIG. 3 shows a micro gas chromatography column, opposite sides of the wall of which are alternately formed with bumps, according to an embodiment of the present invention.

Specifically, when the bumps are formed, as shown in FIG. 3, the ratio of the distance r2 between the top of bumps and the wall of the column and the height r1 of bumps formed on the wall of the column, that is, the r2/r1 ratio, preferably ranges from 1.0 to 1.5. If the r2/r1 ratio is less than 1.0, the size of the bumps becomes excessively large, thus making it difficult to efficiently coat them with a coating material and readily blocking the flow of gas. On the other hand, if the r2/r1 ratio exceeds 1.5, the desired pressure drop does not occur, making it difficult to exhibit superior performance compared to when posts and the like are formed.

Also, as shown in FIG. 3, the ratio of the distance d between bumps and the height r1 of bumps formed on the wall of the column, that is, the d/r1 ratio, preferably falls in the range of 3 to 5. If the d/r1 ratio is less than 3, the bumps are disposed excessively close to each other relative to the height of the bumps, making it difficult to efficiently coat the bumps with the coating material. Furthermore, stagnation regions are formed between the bumps, and thus the contact between the coating material and the gas flow becomes inefficient. On the other hand, if the d/r1 ratio exceeds 5, the distance between the bumps is excessively increased, and a pressure drop may decrease, undesirably deteriorating separation performance.

Meanwhile, the inner wall of the micro gas chromatography column is coated with a stationary phase, and the kind thereof may include at least one selected from among Carbowax, single-walled carbon nanotubes, PDMS (polydimethylsiloxane), and OV-1.

A better understanding of the present invention will be conveyed through the following Examples and Comparative examples, which are merely set forth to illustrate but are not to be construed as limiting the present invention.

Examples

<Manufacturing of Micro Gas Chromatography Column Using MEMS Process>

Figure 4:
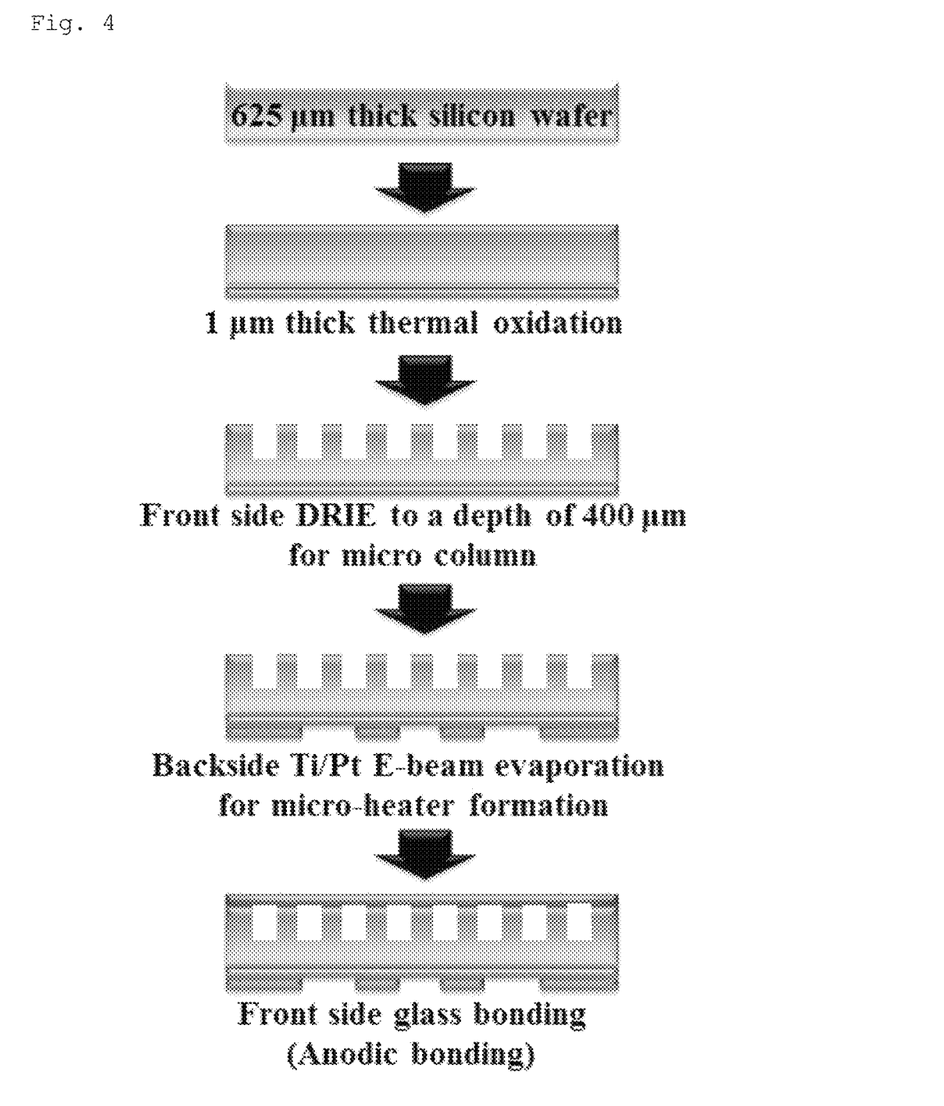
FIG. 4 shows a process of manufacturing a column having posts and a column having bumps using a MEMS process.

As shown in FIG. 4, a column having posts and a column having bumps were manufactured using a MEMS process. $SiO_2$ was deposited on both sides of a 625 μm-thick silicon wafer in (100) orientation through a thermal oxidation process. Thereafter, a positive photoresist was patterned thereon using a lithography process, followed by 400 μm etching using a DRIE (Deep Reactive Ion Etching) process, thereby manufacturing a column.

Specifically, the upper side of the wafer was blocked and the lower side thereof was deposited with Ti, serving as an adhesive layer, at a thickness of 20 nm using an e-beam evaporator, after which platinum for forming an RTD (Resistance Temperature Detector) for detecting the temperature of the column and a heater was deposited to a thickness of 200 nm thereon. Thereafter, the remaining photoresist and the platinum not needed for the pattern were removed using a lift-off process.

Thereafter, as the portion thereof to which the TEC (Thermo-Electric Cooler) has to be attached in order to control heat efficiency and the temperature of the column, the manufactured back side was deposited with an insulating material, $SiO_2$, using PECVD (Plasma-Enhanced Chemical Vapor Deposition), thereby manufacturing a chip. Thereafter, glass was attached to the upper surface of the manufactured chip through anodic bonding, thereby completing a chip-type column.

<Coating of Micro Gas Chromatography Column with Stationary Phase>

In order to coat the inside of the column thus completed with a stationary phase, a coating solution was prepared as follows. Pentane (15 mL), dichloromethane (15 mL), OV-1 (112 mg), and dicumyl peroxide (1 mg) were stirred using a vortex for 30 min. Since the coating solution thus prepared has a boiling point of 30° C., there may take place the situation in which evaporation occurs inside the micro gas chromatography column at the time of injecting the coating solution thereinto using a pump.

With the goal of solving this problem, the chip was fixed at 0° C. using TEC and a heat sink, and was then coated. The column was fully packed with the coating solution, and the inlet and outlet thereof were blocked using septa for a GC column, after which the column was stored at room temperature for about 10 min. Thereafter, the septa were removed from both ends of the column, after which the column was immersed in water at about 50° C. so that the coating solution therein was completely removed through evaporation. In order to stabilize the coating material applied on the wall of the column, the column was heated from room temperature (20° C.) to 200° C. at a heating rate of 1° C./min in an electric furnace, and was then thermally treated at 200° C. for about 2 hr.

Figure 5A:
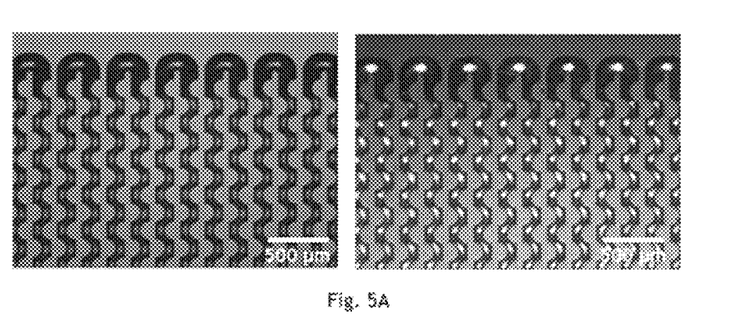
FIGS. 5A and 5B show optical microscope images before and after coating of the column having posts and the column having bumps with a coating material.
Figure 5B:
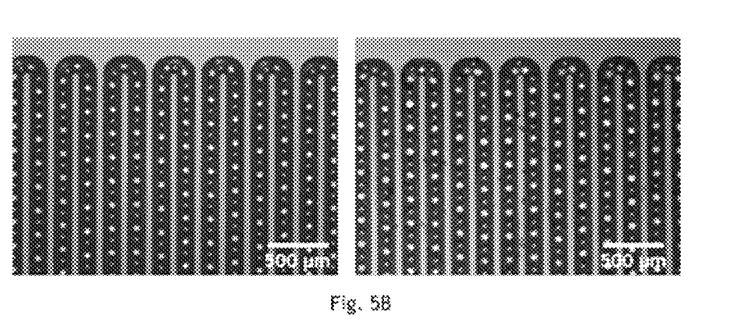

FIGS. 5A and 5B show 5× magnified optical microscope images of the column having the posts and the column having the bumps before and after coating with the coating material. FIG. 5A shows the optical microscope images before (left) and after (right) coating the bump channel-structured micro-column with the separation material, and FIG. 5B shows the optical microscope images before (left) and after (right) coating the post channel-structured micro-column with the separation material.

<Manufacturing of Micro Gas Chromatography Module>

Figure 6:
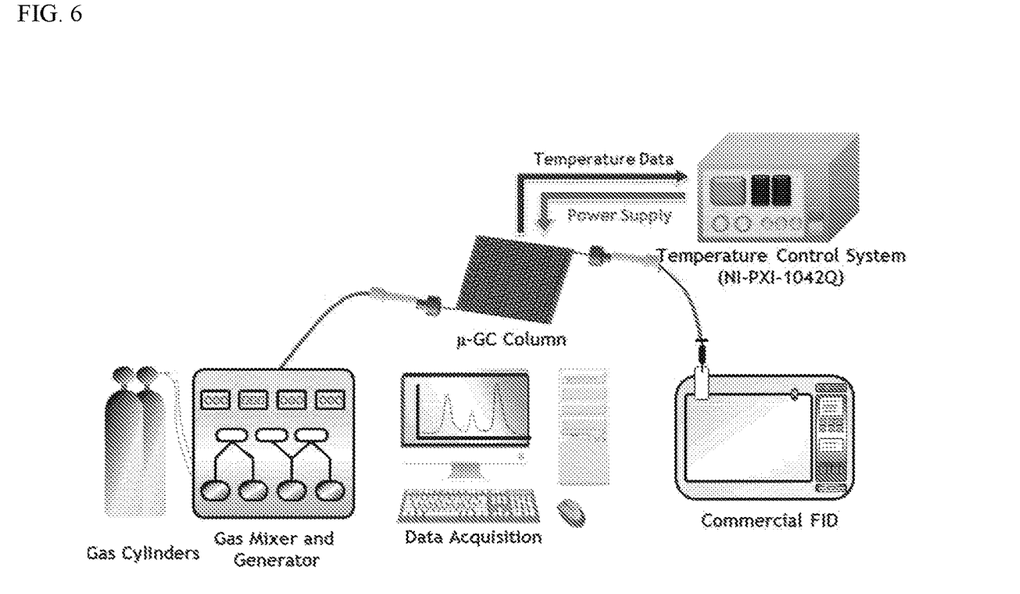
FIG. 6 shows a device setup for a gas separation test of the manufactured micro gas chromatography module.

As shown in FIG. 6, a micro gas chromatography module comprising the micro gas chromatography chip and the PCB module for temperature control was manufactured, and the gas inlet/outlet channel for gas chromatography was formed using a micro gas fitting and a silica-fused capillary tube having a diameter of 360 μm.

<Separation Test of Micro Gas Chromatography Module>

A device setup for a gas separation test of the manufactured micro gas chromatography module is illustrated in FIG. 6. In order to test the separation performance of the manufactured micro gas chromatography module, a gas mixture comprising a total of four components, for example, formaldehyde (37%), benzene (99%), toluene (99%), and ethylbenzene (99%), which were mixed together, was analyzed. The boiling point and molecular weight of each material are given below.

TABLE 1

|  | Formaldehyde (HCHO) | Benzene ($C_6H_6$) | Toluene ($C_7H_8$) | Ethylbenzene ($C_8H_{10}$) |
| --- | --- | --- | --- | --- |
| Boiling Point (° C.) | −19 | 80.1 | 110.6 | 130.6 |
| Molecular Weight (g/mol) | 30.0 | 78.11 | 92.14 | 106.17 |

Here, formaldehyde, benzene, toluene and ethylbenzene are respectively referred to as F, B, T and E. The gas mixture comprising four components was injected into the inlet of the column using a microsyringe, and the gas sample vaporized at the inlet was transferred into the micro gas chromatography column via a carrier gas.

The total amount of the sample that was injected was 0.1 μL, the temperature of the column was 30 to 130° C. (10° C./min), and the sample was transferred into a FID (Flame Ionization Detector) via a carrier gas (mobile phase, helium) at a flow rate of 0.3 SCCM, and the separated gas components were sequentially detected.

The separation test was performed using the bump-structured micro gas chromatography column in which bumps were formed alternately on opposite sides of the wall of the column and using the post-structured micro gas chromatography column in which posts were formed at a regular interval on the wall of the column. Furthermore, under the same analytical conditions for comparison of the micro gas chromatography performance, the separation test was performed in a typical gas chromatography device using a commercially available column.

<Separation Test Results of Micro Gas Chromatography Module>

Figure 7:
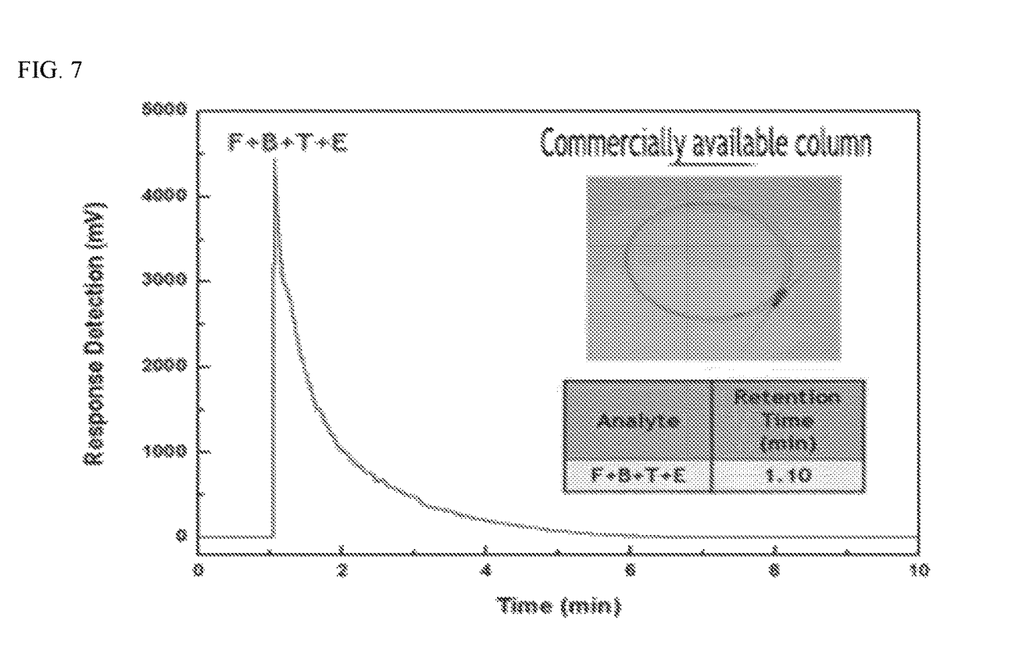
FIG. 7 shows the results of a separation test using a commercially available column (GS-GASPRO, available from AGILENT TECHNOLOGIES), the length of which is cut to 1.5 m, which is the same as the length of the micro-column.

The FBTE gas mixture was subjected to a separation test. FIG. 7 shows the results of the separation test using a commercially available column (GS-GASPRO, available from AGILENT TECHNOLOGIES), the length of which was cut to 1.5 m, which is the same as the length of the micro-column, under the same analytical conditions in order to compare the micro gas chromatography performance.

Based on the results of the separation test of the FBTE gas mixture using the 1.5 m-long commercially available column under the same conditions, as shown in FIG. 7, only one peak appeared at a retention time of 1.10 min, which means that all FBTE components were contained in the single peak, and thus the gas mixture was not separated into individual components but was detected as only one detection signal.

Figure 8A:
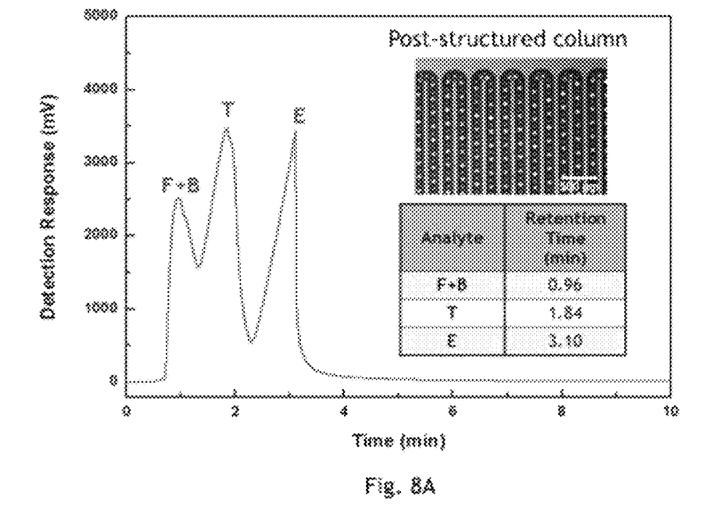
FIG. 8A shows the results of separation of FBTE (Formaldehyde, Benzene, Toluene, Ethylbenzene) using a micro gas chromatography column, the wall of which is formed with a post structure.

Meanwhile, FIG. 8A shows the results of the FBTE separation test using the micro gas chromatography column in which posts are formed on the wall of the column. Here, three peaks appeared at retention times of 0.96, 1.84, and 3.10 min, respectively corresponding to the gas mixture of formaldehyde and benzene, toluene gas, and ethylbenzene gas. When the column having the posts was used, only the three peaks were shown from the introduced gas mixture comprising four gas components, from which the separation performance of the column was regarded as not good. When peaks are analyzed in the detector, formaldehyde and benzene are not separated but are detected together as a single peak, making it impossible to accurately quantitatively and quantitatively analyze the gas mixture.

Figure 8B:
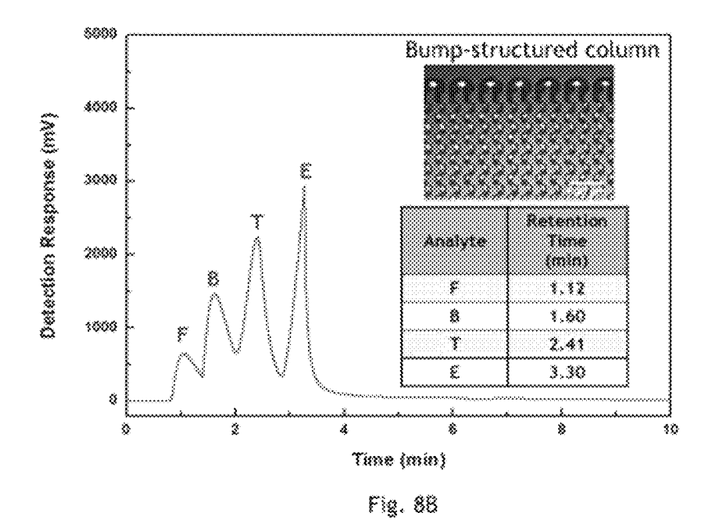
FIG. 8B shows the results of separation of an FBTE gas mixture using a micro gas chromatography column, opposite sides of the wall of which are formed with a bump structure.

On the other hand, FIG. 8B shows the results of separation of the FBTE gas mixture using the micro gas chromatography column in which bumps are formed on opposite sides of the wall of the column. Here, peaks were detected at retention times of 1.12, 1.60, 2.41 and 3.30 min, corresponding respectively to formaldehyde, benzene, toluene and ethylbenzene, from which the gas components contained in the gas mixture were found to be separated and discharged at identifiable retention time intervals.

Therefore, compared to the results of separation tests using the same gas mixture under the same test conditions as shown in FIGS. 7 and 8A, the gas separation performance of the column, which is configured such that the bumps are alternately formed on opposite sides of the wall thereof and in which the extent of pressure drop is the greatest, is significantly high.

Although the preferred embodiments of the present invention have been disclosed for illustrative purposes with reference to the accompanying drawings, those skilled in the art will appreciate that various modifications and equivalents are possible, without departing from the scope and spirit of the invention as disclosed in the accompanying claims. Therefore, the scope of the present invention should be determined by the accompanying claims.

What is claimed is:

1. A separation column for micro gas chromatography, comprising:
   a microchannel formed on a substrate and having any one shape selected from among a rectangular shape, a circular shape, and a serpentine shape; and
   bumps formed on a surface of the microchannel,
   wherein the bumps are alternately disposed to face each other on the surface of the microchannel, and
   a ratio of a distance, r2, between a top of the bumps and a wall of the microchannel to a height, r1, of the bumps formed on the wall of the microchannel, which is r2/r1, ranges from 1.0 to 1.5.

2. The separation column of claim 1, wherein the microchannel has a channel width of 140 to 200 μm and a channel depth of 300 to 450 μm.

3. A separation column for micro gas chromatography, comprising,
- a microchannel formed on a substrate and having any one shape selected from among a rectangular shape, a circular shape, and a serpentine shape; and
- bumps formed on a surface of the microchannel,
- wherein the bumps are alternately disposed to face each other on the surface of the microchannel, and
- a ratio of a distance, d, between the bumps to a height, r1, of the bumps formed on a wall of the microchannel, which is d/r1, ranges from 3 to 5.

* * * * *